United States Patent [19]

Marcucci

[11] Patent Number: 4,968,633

[45] Date of Patent: Nov. 6, 1990

[54] MUCOSAL ALLERGO-TEST AND RELEVANT DEVICE FOR THE DETERMINATION OF SPECIFIC AND TOTAL IgE

[76] Inventor: Francesco Marcucci, No. 15, Via Brunamonto, 06100 Perugia, Italy

[21] Appl. No.: 62,465

[22] PCT Filed: May 9, 1986

[86] PCT No.: PCT/IT86/00036

§ 371 Date: May 26, 1987

§ 102(e) Date: May 26, 1987

[87] PCT Pub. No.: WO87/02465

PCT Pub. Date: Apr. 23, 1987

[30] Foreign Application Priority Data

Oct. 15, 1985 [IT] Italy .................... 48671 A/85

[51] Int. Cl.⁵ ................ G01N 33/563; G01N 33/548
[52] U.S. Cl. ......................................... 436/513; 435/7;
435/805; 436/518; 436/810; 422/56; 422/57;
422/58; 424/434; 424/435; 424/436; 424/437;
424/9
[58] Field of Search ............ 435/7, 805; 436/513,
436/518, 810; 422/56–58; 424/434–437, 9 T

[56] References Cited

U.S. PATENT DOCUMENTS

| 3,509,872 | 5/1970 | Truhan | 422/58 |
| 3,941,876 | 3/1976 | Marinkovich | 436/513 |
| 4,294,817 | 10/1981 | Burgett et al. | 422/58 X |
| 4,454,226 | 6/1984 | Ali et al. | 436/513 X |
| 4,459,360 | 7/1984 | Marinkovich | 436/513 |
| 4,587,099 | 5/1986 | Rothe et al. | 422/56 |

FOREIGN PATENT DOCUMENTS 8502262 5/1985 PCT Int'l Appl. .

Primary Examiner—Esther L. Kepplinger
Assistant Examiner—Carol A. Spiegel
Attorney, Agent, or Firm—Richard Bushnell

[57] ABSTRACT

An allergological test for detecting an allergic condition, said test consisting in contacting the mucous membrane direct with the allergen or the anti-IgE antibody linked to a solid phase, so that a rapid in situ incubation is obtained of the allergen or of the anti-IgE antibody with the mucous membrane antibodies, and in the successive in vitro determination of the specific or total IgE through radioimmunological or immunoenzymatic procedures. Said testing procedure is carried out by employing a plastic material application device comprising one or more receptacles or housing in which some supports are inserted, such supports bearing allergens or anti-IgE antibodies linked to the supports themselves. Said testing procedure can also be employed for performing a particular test of specific challenging.

5 Claims, 3 Drawing Sheets

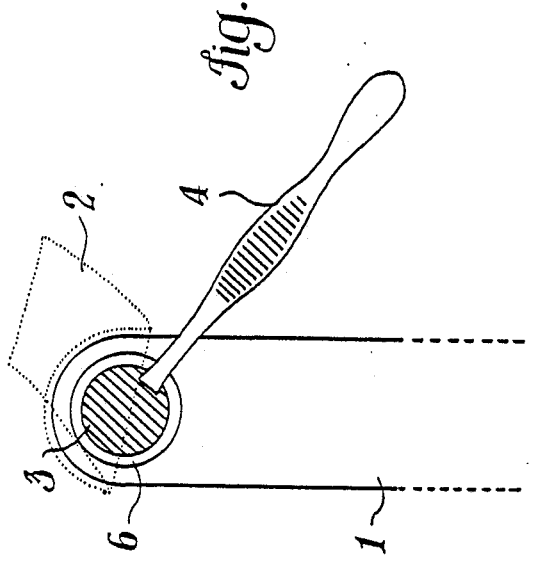
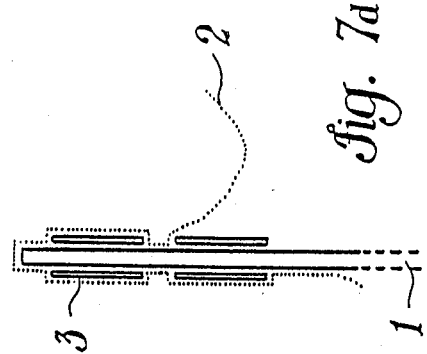
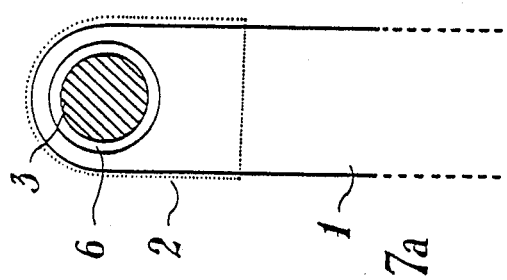
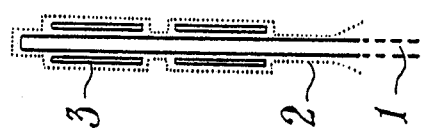

MUCOSAL ALLERGO-TEST AND RELEVANT DEVICE FOR THE DETERMINATION OF SPECIFIC AND TOTAL IgE

The present invention relates to a mucous membrane allergy immunoassay test as well as to a device for carrying out said test for the in situ detection of specific and total IgE. More particularly, this invention relates to an allergy immunoassay test in which, by means of an application device, the allergen or the anti-IgE antibody, both linked to a support, are contacted direct with the mucous membrane, preferably with the nasal mucous membrane, performing an in situ incubation with the mucous membrane IgE, after which the in vitro determination is carried out of the specific and total IgE. Moreover, said testing procedure and the device for carrying out the same, also allow to perform simultaneously a particular test of specific challenging, for instance a specific challenging nasal test.

As is well known, at the present state of the art, the diagnosis of allergic diseases is performed through the following fundamental tests.

A—skin tests
B—determination of the amounts of immunoglobulins E (IgE) in the blood
C—specific challenging tests.

Skin tests (A) consist in the application of the suspected allergens on the skin of the patient, for example by pricking or scratching; in that way a local reaction is stimulated (reddening and swelling), which reaction is produced by the linking of the allergen with the IgE.

The in vitro determination of the amount of the IgE in the blood of the patient (B), the blood being drawn by pricking a vein, is carried out through radioimmunological or immunoenzymatic methods. Such quantitative determination consists in contacting the serum of the patient in vitro with a support bearing the allergen or the anti-IgE antibody linked to itself, and in the successive determination of the IgE of the patient which become linked to the same.

The specific challenging tests (C) consist mainly in provoking the nasal, ocular or bronchial symptomatology etc. contacting such mucous membrane surfaces directly with the suspected allergens which can be administered for instance in the form of a spray, aerosol, or by installation and so on.

After the clinical investigation, the skin tests (A) form the first diagnostic approach, which can be replaced by the quantitative determination (B) of the specific IgE in the serum in the case of impossibility of performing the skin tests or anyway in the case of diagnostic doubts.

If that second investigation also gives no satisfying results, specific challenging or provoking tests (C) can be carried out.

Such diagnostic procedures show some limitations which in the case of skin tests consist in:

a—impossibility of performing the test in the case of patients suffering from spread skin diseases (serious eczema, urticaria);
b—falsely positive result of the test due to the employment of unsuitable allergenic extracts (poor purification, excessive concentration) or to the absence of effective aetiological meaning (preclinical, subclinical or postclinical allergy);
c—falsely negative result of the test which can occur during an antiallergic treatment, for example with antihistaminic compounds, in the case of a reduced skin reactivity (for instance in the early childhood or in old patients or in patients with hyperpigmented skin or with the skin seriously affected with Lichen), because of the presence of the immunoglobulins E at the mucous membrane surfaces level only and not in the skin and the blood, or otherwise because of the degradation of the allergenic extracts;
d—poor acceptance and difficulties in carrying out the procedure in the case of patients in their early childhood, as the testing procedure is relatively painful and asks for some cooperation on the patient's part;
e—possibility of inducing, though rarely, serious general reactions (anaphylactic shocks) as a result of the absorption of the allergen into the circulatory system.

In the cases mentioned above, and anyway when there is no agreement between the clinical suspicion and the skin tests (A), it is necessary to perform the quantitative determination (B) of the amounts of the specific and total IgE in the serum.

That second procedure gives the advantages of a high sensitivity, a good standardization and a good reproducibility of the results, together with the absence of risks for the patient and the possibility of quantitatively determining the immunoglobulin E levels.

The two procedures (i.e., the skin tests and the quantitative determination of the specific IgE in the serum) give results that can be correlated to each other in the 60–90% of the total cases according to the different allergens.

However such procedure is not free from limitative drawbacks, and in particular:

a—long times are needed for carrying out the method;
b—there is the possibility of falsely positive results due to impurities present in the allergens which link the IgE not immunologically, and/or due to the presence of high levels of total IgE which become linked to the allergens non-specifically
c—there is the possibility of falsely negative results because other immunoglobulins (IgE), present in the blood in amounts remarkably higher than the IgE amounts, may become linked to the allergen, so preventing the IgE from becoming linked to the same and thus from being detected and identified. The falsely negative result of the test may also occur in the case of "low degree" allergies or otherwise in the case of IgE localization exclusively at the mucous membrane surfaces which are affected with the disease;
d—the impossibility may occur of performing the test in the case of patients refusing drawing of blood or in the case of children when the drawing of blood may be particularly difficult.

The challenging or provoking tests (C) are employed on the contrary when some diagnostic doubts occur further to the two other tests.

Such tests are in agreement with the results of the quantitative determination of the specific IgE in the serum and of the skin tests in 80% of the total cases and they can give diagnostic results in 5–10% of the cases in which the two other tests give doubtful results.

Moreover, they give the advantage of the detection of the target organ condition (which condition is not necessarily analogous to the skin or the serum condition). They are also useful in the study of the efficiency of the preventive drugs as well as in the study of the effects of immunotherapy.

However, such provoking or challenging tests show some important drawbacks consisting in:

(a) the need for a normal basic condition for carrying out the test;

(b) the need for the previous interruption of drug administration (corticosteroids, bronchial dilating drugs, DSCG Di Sodium Chromo Glycate);

(c) time wasting;

(d) troubles for the patients;

(e) possibility of falsely positive results because of aspecific reactivity or possibility of falsely negative results because of too low doses of the allergen employed;

(f) the employment of costly apparatus;

(g) impossibility of performing the test in the case of non cooperating patients pediatric patients);

(h) the risk due to the possibility of evoking serious allergic reactions.

Summarizing the considerations mentioned above, it can be set forth that the main limitations of the commonly employed diagnostic procedures are represented;

A—by the possibility of falsely positive results which are estimated to be about 25% both for the skin tests and for the quantitative determination of the specific IgE;

B—by the possibility of falsely negative results which are estimated to be of the order of 20% both for the skin tests and for the quantitative determination of the specific IgE;

C—by the difficulties of performing and of standardizing the provoking or challenging tests and by the possibility of aspecific responses of said tests.

In an attempt at obviating such problems, a number of studies have been performed in the biological liquids that wet the mucous membranes, with the aim of determining the amounts of the IgE, which can be found mainly within said sites where they are the direct cause of the pathological process underlying the allergic diseases.

The special interest offered by such investigations consists in that the specific antibodies that can be found on the mucous membranes are an actual expression of the pathological process in progress.

Indeed, such antibodies may also be undetectable at the skin or the serum levels as they are confined to the mucous membrane surface only, whereas in skin or serum specific immunoglobulins E can be present, which IgE are not responsible for the disease in progress, but for a previous condition or for a subclinical stage of the disease.

Results obtained from such investigations up to the present time can be considered interesting from the research viewpoint only, but not from the point of view of their application to the clinical diagnosis, because of problems connected to difficulties in drawing suitable samples, as well as to the degradation of the IgE and the standardization and the reproducibility of data obtained with biological liquids.

Indeed, the IgE contained within the mucous secretions can undergo degradation processes of their molecules so that the quantitative determination of the same is poorly reliable.

The drawing of such secretions may ask for the introduction of solutions for mucous membrane washing, which solutions interfere with the concentration of the native secretions in a way that is hardly determinable accurately.

The quantitative determination of the reference compounds such as proteins or salts, which determination is employed for obtaining the actual concentration of the immunoglobulins E, does not allow to overcome the problem connected to the variability of the composition of the mucous secretion liquids.

Samples drawn from the mucous membranes contain coarse matter such as for instance mucous membrane parts, cellular debris etc., which make it necessary to carry out purification processes, for example filtration, centrifugation, fractionation. Such procedures, in addition to the concentration processes, which are necessary to obtain IgE amounts suitable for quantitative determination, can give rise to losses of the immunoglobulins as well as to alterations in the molecular structures of the same.

Thus, it is well evident that it is important to have at disposal an allergy immunoassay test and a means by which the detection of the immunoglobulins E is performed direct on the mucous membrane surfaces.

Indeed, employing such a procedure, the limitations of the procedures employed at the present time are overcome, by realizing with one intervention only the advantages of at least two of them (quantitative determination of the amounts of the specific IgE and the specific challenging or provoking test).

Advantageously the difficulties are removed inherent to the quantitative determination of the amounts of the IgE in the secretion liquids, as the allergen-specific immunoglobulin E bond is realized according to the present invention direct on the mucous membrane surfaces, and in a specific way on the nasal mucous membranes. Thus, according to the fundamental characteristic of the present invention, the incubation of the allergen with the mucous membrane IgE occurs in situ, so excluding the need for the in vitro incubation of the allergen with the IgE contained in such samples, as is the case with blood or biological samples.

According to the present invention, the means mentioned above consist of a device through which one or more supports are contacted direct with the mucous membrane such as for instance the nasal, the ocular, the rectal mucous membrane and so on, the allergens or the anti-IgE antibodies being previously linked to said supports.

The inventive technology so outlined above allows to obtain a number of advantages with respect to the usual procedures mentioned, and more exactly such advantages are:

the easy and rapid procedure of the test, which is performed in a time shorter than or at most equivalent to the time needed for carrying out the skin tests;

the very high acceptance on the patient's part of any age as the testing procedure is absolutely bloodless and painless;

the possibility of performing the test at any moment during the day, as the procedure does not require that the patient be fasting;

the absence of interferences due to the concomitant use of antiallergic drugs;

the absence of risks for the patient as the allergen can be immediately and completely removed;

the possibility of performing the test also with patients suffering from widely spread dermatitis or from a very high skin reactivity (falsely positive tests) or from a reduced skin reactivity (for example in the case of patients in their early childhood) (falsely negative results);

a higher specific character with respect to the skin tests and to the quantitative determination of the amounts of the IgE in the serum as said IgE are present at that level (the serum and the skin) secondarily with respect to their presence in the mucous membranes, where they are responsible for the disease;

a higher reliability with respect to the quantitative determination of the amounts of the specific IgE in the serum as the rapid in situ incubation is not affected by the presence of high amounts of IgG immunoglobulins;

the possibility of including into a single operation the determination of the specific IgE and the specific challenging or provoking test;

a higher reliability with respect to the specific challenging or provoking tests as the test of the invention allows to check non-specific possible responses through the successive determination of the specific IgE by means of the same support.

In order to satisfy the needs mentioned above, the present invention suggests as its specific object a mucous membrane allergy immunoassay test for the in situ determination of the specific as well as of the total IgE, which test is characterized in that it comprises the following operations:

(a) contacting with a mucous membrane surface at least a support to which an allergen or an anti-IgE antibody has been linked;

(b) keeping said support adherent to the mucous membrane for a time sufficient to realize an in situ incubation with the formation of a link between the IgE present on the mucous membrane surfaces and said allergen or said anti-IgE antibody;

(c) recovering said support, and inserting the same into a testtube and the performing the radioimmunological or immunoenzymatic quantitative determination of the amounts of the total and specific IgE.

More particularly, said mucous membrane surface is the nasal, the conjunctival, the rectal membrane, the nasal mucous membrane being preferable.

By preference said period of in situ incubation can be variable from less than one minute to about 20 minutes.

Advantageously said quantitative determination of the amounts of the specific or total IgE, can be carried out on the support after storing the same for a period variable up to 4 months and at a temperature of about $-20°$ C.

As already mentioned above, the test according to the present invention can be employed as regards its two stages (a) and (b) also for a specific challenging or provoking test, in particular the nasal provoking test (NPT) contacting with the mucus on the mucous membrane surface a support to which no allergen has been linked (negative control) and next a support to which the test allergen has been linked.

As said allergen is insoluble and strongly linked to the support, it evokes a feeling of itch which is limited to the contact area that can be subjectively detectable by the patient. The provoking test therefore does not give any risk of undesired reaction as can occur in the case of free allergens which can be largely absorbed by the mucous membranes or which can be deeply inhaled. Thus the test of the present invention does not ask for a physician for performing the same and for evaluating its results.

Moreover, the present invention also comprises the device for the in situ determination of the total or specific mucous membrane IgE, said device being characterized in that it is made up of suitable means for fastening said support and for realizing the contact with the mucous membrane surface. More particularly, in the special case of placing said device into the endonasal mucous membrane, the device consists of a thin, rounded ends and edges rod, on which rod at least a receptacle is fastened, said receptacle being made up of a permeable matter and designed for housing said support. The receptacle can be present on both surfaces of said rod.

Preferably said thin rod is made up of a plastic, paper or rubber material. Said thin rod can advantageously bear some openings or windows in order to lay open the solid phase at the maximum degree.

Said receptacle is advantageously made up of one or two sheets which are closed along their edges for their whole perimeter except for an open segment for the introduction of the support, said open segment being closed after introducing said support, for instance in some cases by means of a tab which can be bent and can be opened by tearing.

More particularly, the receptacle consists of a man-made fiber.

It is to be observed that according to the present invention said receptacle is designed aiming at:

making it possible to contact the support with the mucous membrane so as to allow the link between the mucous membrane IgE and the allergen or the anti-IgE antibody to form;

preventing the mucous matter or other biological matter from adhering to the support (to which the allergen or the anti-IgE antibody is bonded) which biological or mucous matter would ask for drastic procedures for being removed, as already mentioned above;

preventing the support to which the allergen or the anti-IgE anti-body is bonded from being inhaled or expelled.

It is well clear that said support can be made up of any material (a polymeric material) which is water insoluble and suitable for forming a stable bond with the allergen or the anti-IgE-antibody, such as for instance: paper, Sephadex, polystyrene, polyvinyl or other materials.

The support can be of any shape, and it is preferably of a planar or oval shape, for instance. The shape of the support is to be such as to allow its insertion into the receptacle disclosed above. The whole device is to be necessarily sterile and non-toxic. The determination procedure in which the means according to the present invention is employed can include the employment of reference standards previously subjected to incubation. Said reference standards are obtained by incubating the support to which the allergen or the anti-IgE-antibody is bonded with a serum containing a known amount of the specific IgE for that allergen or of total IgE; said serum is employed in four suitable concentrations in order to obtain a reference curve.

After suitable washing, for example with 0.9% sodium chloride, the preincubated reference standards consisting of the support+allergen +IgE or the support+anti-IgE+IgE, can be stored at $-20°$ C. for a period of time from 0 to 4 months or they can be employed immediately.

The present invention will be disclosed in the following for illustrative and not for limitative purposes with particular reference to the enclosed drawings, wherein:

FIGS. 7a and 7b show a second arrangement of the device according to the present invention; and FIGS. 7c and 7d show a third arrangement of the device according to the present invention.

With reference now to the Figures mentioned above, the thin rod can be observed, pointed out by 1, of the application device, said rod having the upper ends rounded, to which a receptacle 2 is fastened or applied for housing the support 3.

Figure 3:
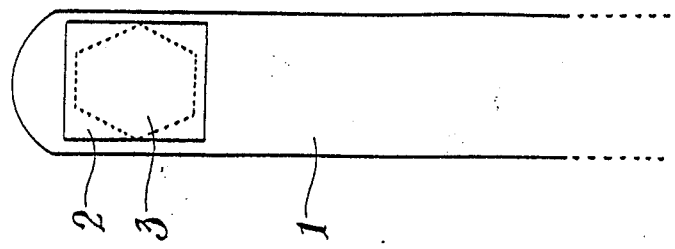
FIGS. 2 and 3 show respectively said support as partially or fully inserted into the receptacle.
Figure 2:
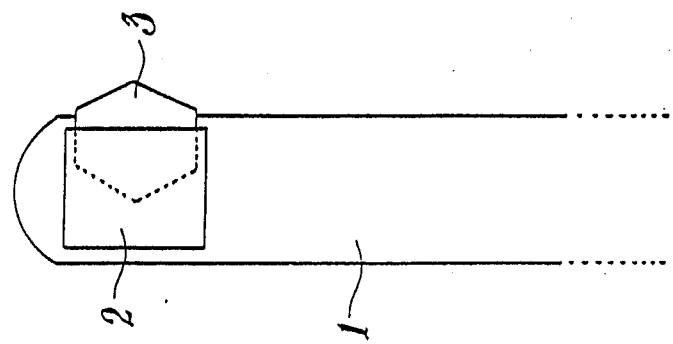
Figure 1:
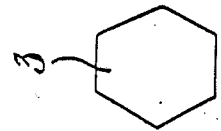
FIG. 1 shows the thin rod, the receptacle of first means according to the present invention and the support employed.
Figure 1:
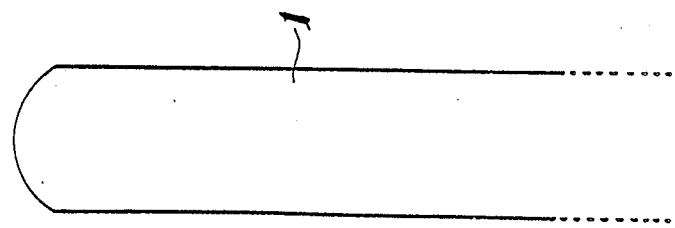
Figure 6:
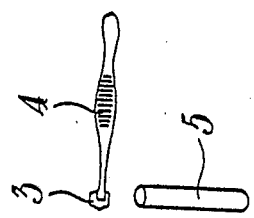
FIG. 6 shows the insertion of said support into the test-tube inside.
Figure 5:
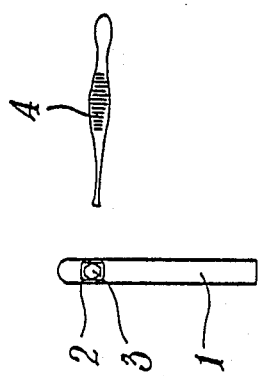
FIG. 5 shows the thin rod extracted together with the support to which the IgE is linked.
Figure 4:
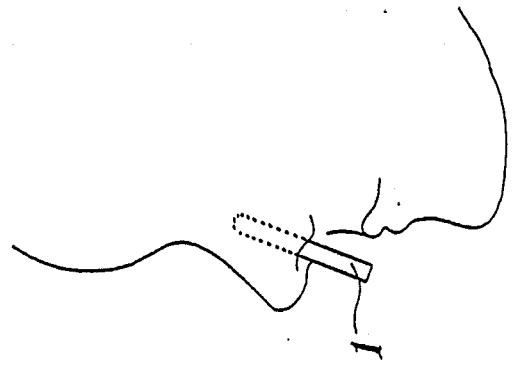
FIG. 4 shows the endonasal application of said thin rod.

In FIG. 4 the thin rod can be observed as applied into the endonasal cavity, said rod being successively extracted from the same after the necessary incubation period (see FIG. 5).

After removal of the support 3 from the rod 1 by means of the tweezers 4, said support is introduced into the test-tube 5 before storing the same or it is immediately employed for the radioimmunological quantitative determination or for the immunoenzymatic quantitative determination of the amounts of the specific or total IgE.

FIG. 7a and 7b relate to an alternative embodiment which is preferred and in which the thin rod 1 shows an opening or window at 6 for allowing the solid phase (support 3) to be exposed at a higher extent and said supports 3 can be extracted from the receptacles which consist of the permeable membrane 2 by means of a tearing opening action (FIG. 7b).

FIGS. 7c and 7d show a further preferred arrangement of the device according to the present invention, in which a thin rod 1 supplied with the receptacles 2 bears the pairs of supports 3 housed within said receptacles. In that case, the extraction of the support 3 is performed in the same way by tearing the receptacle 2 (FIG. 7d). Next the testing procedure is carried out as mentioned above.

The reliability and the specificity of the results obtained by the procedure according to the present invention are proved by data obtained in the experiments disclosed in the following which relate to 30 control normal subjects and to 62 patients suffering from allergic diseases of the respiratory organs (rhinoconjunctivitis and bronchial asthma) (see Table 2).

PATIENTS AND METHODS

The New Test (N.T.) for the determination of nasal IgE was carried out on 16 children suffering from rhinitis (R) and/or conjunctivitis (C) or asthma (A), both of the seasonal (s) and of chronic (c) as well as in 30 control subjects which were non-atopic, healthy and from 1 to 14 years old (Table 2).

Taking into account the functional and the anatomic differences in the nasal membrane, the test variation was performed in two successive samples obtained from the right and the left nostril, after the same incubation period, the device being placed in the same zone of the nasal mucous membrane. In order to determine the differences between the N.T. and the testing procedures employed at the present time for the determination of the IgE on the mucous membrane surface, the quantitative determination was performed of the specific IgE in 7 patients in the native, undiluted nasal secretion also. The samples were subjected to the same incubation periods (2, 15, 10 and 30 minutes) and then they were compared.

In 6 cases the nasal specific IgE were determined employing two different solid phases (polystyrene and paper) linked to the allergen of interest.

The N.T. for the total nasal IgE was carried out in 33 patients and 20 healthy, non-atopic control subjects.

In all patients whose anamneses or clinical histories has been accurately considered, the skin prick test (SPT) and the quantitative determination of the specific IgE in the serum as well as in the nasal mucous membrane were carried out.

The allergens were selected on the basis of the anamnesis.

The SPT's performed with allergen extracts from the Pharmacia were evaluated by comparison of the allergen reaction with the reaction to histamine with the following results: +++ identical with the histamine; ++ 50% of the reaction to histamine; ++++ twice the reaction to histamine.

The specific IgE in the serum were determined by means of the Phadezym RAST Pharmacia. Values higher than 0.35 PRU/ml were considered positive. The total IgE were determined by means of the Phadezym PRIST Pharmacia.

The nasal IgE were obtained after an in situ incubation by the method already disclosed above (N.T.).

For the determination of the total and of specific nasal IgE paper disks were also employed linked to allergen or to the anti-IgE antibody from the Pharmacia and the Pharmacia reagents for the Phadezym RAST and the Phadezym PRIST tests. In 6 cases the polystyrene solid phase was also employed linked to the allergen (LOFARMA). The nasal and the serum samples were tested on such occasion.

RESULTS

Data obtained in the variation test carried out taking into account the anatomic and the functional differences in the surfaces of the nasal mucous membrane, such changes being expressed as the percentage changes in the absorbance (420 nm) were within the range from 6% to 32% ($\overline{X} \pm SD = 19 \pm 13$).

Such data show a good reproducibility of the N.T.

The comparison between the N.T. and the in vitro test performed in the native undiluted nasal secretion showed a significant increase in the values from 2 to 5 minutes in the N.T. only (Table 1). Moreover, in all samples the N.T. showed values remarkably higher than the values relative to the nasal secretions (NS); indeed, the average percentage in the variation was respectively of 65%, 78.9%, 76%, 72.4% in the case of samples kept in incubation for 2,5, 10 and 30 minutes (Table 1).

The N.T. shows a sensitivity significantly higher with respect to the in vitro determination of the amounts of the specific IgE in the native undiluted secretions.

The nasal specific IgE determined by means of two different solid phases (paper and polystyrene) showed results in agreement as expressed in RAST score (classes 1, 2, 3 and 4) (Table 3).

The N.T. was concordantly positive with the specific IgE in the serum in 46/62 patients (74.2%); concordantly negative in 10/62 patients (16.1%). In all, 56 concordant cases found out of 62 (90.3%). The N.T. gave positive results also in 5 cases which were negative for the serum (8.1%) (Table 2).

The N.T. was concordantly positive with the skin prick test (SPT) in 46 out 62 cases (74.2%); it was concordantly negative in 9 out 62 cases (14.5%). In all, 55 concordant cases were found out of 62 (88.7%).

The N.T. gave positive results also in 4 cases with negative SPT (6.4%) (Table 2).

As regards allergens, the comparison between the specific IgE in the serum and the N.T. had given the following results:

Concordantly positive tests for the allergens, 79/195 (40.5%);

Concordantly negative tests for the allergens 73/195 (37.4%).

In all, 152 concordant values for the allergen were found out of 195 cases (77.9%).

The positive values for allergens in the serum only were found to be 11/195 (5.7%) and those which were positive with the N.T. only were found to be 32/195 (16.4%) (Table 2).

As regards the allergens, the comparison between the skin prick test and the N.T. gave the following results:

Results were concordantly positive for the allergens in 86 out of 195 cases (44.1%);

results were concordantly negative for the allergens in 68 out of 195 cases (35.4%).

In all, values were in agreement for the allergens in 155 out of 195 cases (79.5%).

Values which were positive for the allergens with SPT only were 15 out of 195 (7.7%) and those which were positive with the N.T. only were 25 out 195 (12.8%) (Table 2).

To sum up, the results of the N.T. can be considered as reliable because of the significative agreement with the determination of the amounts of the specific IgE in the serum and with the skin prick test.

Moreover, the N.T. shows a higher sensitivity with respect to the determination of the specific IgE in the serum; as a matter of fact, 5 cases (8.1%) and, as regards the allergens, 32 cases (16.4%) gave positive results with N.T. only, in agreement with the anamnesis.

The statistical evaluation of the data obtained in the serum and the N.T. showed a significative positive correlation ($r = 0.786$ and $P \leq 0.0001$).

In the case of 30 healthy non-atopic control subjects, 5 fundamental allergens (Dermatophagoides P. Lolium p., Parietaria O., Egg white and Cow milk) gave negative results in all cases.

Data so obtained showed the high specificity of the N.T.

In the case of 24 patients out of 33, the total IgE examined by the N.T. showed positive values ($>0.5$ IU/ml) (Table 4).

The total IgE in the serum gave high values in 28/33 cases.

Results were in agreement in 29 cases (87.8%). In the case of 19 out of 20 healthy non-atopic control subjects, the total IgE examined with the N.T. were negative.

The reliability as well as the specificity of the N.T. for the determination of the amounts of the total IgE were put into evidence by the good correlation with the values obtained for the total IgE in the serum (87.7%) and by the very high number of negative results in the control (95%).

As a concluding remark, the N.T., in addition to the reproducibility, specificity and sensitivity features mentioned above, shows advantageous with respect to the tests employed at the present time, as it is free from risks and bloodless, and it is so easy to perform as to allow the patient to carry out the same by himself and next to send it to the laboratory.

The specified abbreviations employed in the following tables 1-2g are defined as follows:

| | |
|---|---|
| N.T. | Nasal Test |
| N.S. | Nasal Secretion |
| SPT. | Skin Prick Test |
| PRU. | Phadebas Rast Uniteit |
| A.C. | Chronic Asthma |
| R.C. | Chronic Rhinitis |
| RC.s. | Seasonal RhinoConjuntivitis |
| RC.c. | Chronic RhinoConjuntivitis |
| A.S. | Seasonal Asthma |
| R.S. | Seasonal Rhinitis |
| C.c. | Chronic Conjunctivitis |
| E. | Eczema |
| Partiet. | Parietoria (Pellitory) |
| Altern. | Alternaria |
| Asperg. | Aspergillus |

TABLE 1

| | Allergens | t. | N.T. | N.S. |
|---|---|---|---|---|
| B.M. | G 5 | 2' | 3.54 | 0.36 |
| | | 5' | 6.76 | 0.63 |
| | | 10' | 4.23 | 0.7 |
| | | 30' | 2.8 | 0.58 |
| M.F. | D 1 | 2' | 3.5 | 5.13 |
| | | 5' | >17.5 | 6.57 |
| | | 10' | >17.5 | 6.8 |
| | | 30' | >17.5 | 7.43 |
| P.M. | G 5 | 2' | 17.11 | 4.06 |
| | | 5' | >17.5 | 4.1 |
| | | 10' | 16.27 | 4.15 |
| | | 30' | >17.5 | 7.24 |
| L.L. | G 6 | 2' | 7.66 | 1.4 |
| | | 5' | 10.53 | 1.9 |
| | | 10' | 11.6 | 4.06 |
| | | 30' | 9.83 | 2.68 |
| L.E. | T 9 | 2' | 1.22 | 2.1 |
| | | 5' | 6.86 | 1.8 |
| | | 10' | 6.9 | 1.71 |
| | | 30' | 7.35 | 1.77 |
| S.G. | D 1 | 2' | 2.04 | 0.67 |
| | | 5' | 3.78 | 0.69 |
| | | 10' | 3.5 | 0.69 |
| | | 30' | 3.6 | 0.84 |
| B.F. | G 6 | 2' | 2.75 | 0.9 |
| | | 5' | 4.61 | 0.6 |
| | | 10' | 4.7 | 0.35 |
| | | 30' | 4.68 | 0.64 |

TABLE 2a

| Case | Symptomatology | Allergen | SPT | IgE in the serum PRU/ml | Classes | Nasal IgE PRU/ml | Classes |
|---|---|---|---|---|---|---|---|
| M.E. | A.c. | Dermat. P. | ++++ | >17.5 | 4 | >17.5 | 4 |
| | | Lolium P. | ++− | <0.35 | 0 | <0.35 | 0 |
| | | Pariet. O. | −−− | <0.35 | 0 | <0.35 | 0 |
| S.M. | A.c. | Dermat. P. | ++− | >17.5 | 4 | 7.28 | 3 |
| | R.c. | Lolium P. | +++ | 1.53 | 2 | 1.54 | 2 |
| R.A. | RC.s. | Lolium P. | ++++ | 5 | 3 | 7.00 | 3 |
| | | Dermat. P. | −−− | <0.35 | 0 | <0.35 | 0 |
| F.A. | RC.c. | Dermat. P. | ++++ | >17.5 | 4 | 8.1 | 3 |

TABLE 2a-continued

| Case | Symptoma-tology | Allergen | SPT | IgE in the serum PRU/ml | Classes | Nasal IgE PRU/ml | Classes |
|---|---|---|---|---|---|---|---|
| | | Dermat. P. | ++++ | >17.5 | 4 | 2.39 | 2 |
| | | Lolium P. | ++− | 9.47 | 3 | 4.61 | 2 |
| | | Pariet. J. | ++− | <0.35 | 0 | <0.35 | 0 |
| F.P. | A.c. | Lolium P. | +++ | >17.5 | 4 | 1.13 | 2 |
| | RC.c. | Dermat. P. | ++− | >17.5 | 4 | 10.6 | 3 |
| | | Cynodo. D. | ++− | 2.2 | 2 | 0.63 | 1 |
| | | Pariet. O. | − − − | <0.35 | 0 | <0.35 | 0 |
| C.A. | A.c. | Phleum P. | ++++ | >17.5 | 4 | 9.25 | 3 |
| | RC.c. | Dermat. P. | +++ | >17.5 | 4 | 8.63 | 3 |
| | | Pariet. J. | − − − | <0.35 | 0 | <0.35 | 0 |
| T.E. | A.s. | Phleum P. | ++++ | >17.5 | 4 | >17.5 | 4 |
| | RC.s. | Artemi. V. | ++− | 1.9 | 2 | 0.88 | 2 |
| | | Olea Eur. | ++− | 2.6 | 2 | 1.2 | 2 |
| | | Dermat. P. | ++− | 3.4 | 2 | 1.17 | 2 |
| | | Pariet. J. | − − − | 1.45 | 2 | 1.26 | 2 |
| A.D. | R.c. | Dermat. P. | +++ | >17.5 | 4 | 10.24 | 3 |
| | | Pariet. J. | − − − − | <0.35 | 0 | <0.35 | 0 |

TABLE 2b

| Case | Symptoma-tology | Allergens | SPT | IgE in the serum PRU/ml | Classes | Nasal IgE PRU/ml | Classes |
|---|---|---|---|---|---|---|---|
| N.F. | A.s. | Phleum P. | ++++ | >17.5 | 4 | >17.5 | 4 |
| | R.s. | Taraxa. V. | +++ | 0.73 | 2 | <0.35 | 0 |
| | C.c. | Planta. L. | +++ | <0.35 | 0 | 0.79 | 2 |
| | | Pariet. O. | +++ | 2.1 | 2 | 1.7 | 2 |
| | | Dermat. P. | ++++ | <0.35 | 0 | 0.43 | 1 |
| | | Populus | +− − | <0.35 | 0 | <0.35 | 0 |
| B.F. | A.c. | Dermat. P. | ++− | 2.8 | 2 | <0.35 | 0 |
| | | Pariet. O. | − − − | <0.35 | 0 | <0.35 | 0 |
| | | Altern. T. | − − − | <0.35 | 0 | <0.35 | 0 |
| R.E. | A.c. | Dermat. P. | − − − | <0.35 | 0 | 0.55 | 1 |
| | R.c. | Pariet. J. | − − − | <0.35 | 0 | 1.25 | 2 |
| B.B. | A.s. | Cynodo. D. | − − − | <0.35 | 0 | 0.6 | 1 |
| | R.s. | Poa Prat. | − − − | <0.35 | 0 | 0.5 | 1 |
| | | Pariet. O. | − − − | <0.35 | 0 | <0.35 | 0 |
| S.F. | A.c. | Dermat. P. | − − − | <0.35 | 0 | 0.37 | 1 |
| | E. | Pariet. J. | − − − | <0.35 | 0 | <0.35 | 0 |
| R.S. | R.c. | Dermat. P. | ++− | <0.35 | 0 | <0.35 | 0 |
| | C.c. | Dermat. F. | +++ | <0.35 | 0 | <0.35 | 0 |
| | | Pariet. J. | − − − | <0.35 | 0 | <0.35 | 0 |
| M.G. | R.c.s. | Dermat. P. | − − − | 0.38 | 1 | 0.45 | 1 |
| | | Pariet. J. | − − − | <0.35 | 0 | 0.35 | 1 |
| | | Altern. T. | − − − | <0.35 | 0 | <0.35 | 0 |
| C.MR. | R.c. | Pariet. J. | − − − | <0.35 | 0 | <0.35 | 0 |
| | | Dermat. P. | − − − | <0.35 | 0 | 0.53 | 1 |
| | | Asperg. F. | − − − | <0.35 | 0 | 0.36 | 1 |

TABLE 2c

| Case | Symptoma-tology | Allergens | SPT | IgE in the serum PRU/ml | Classes | Nasal IgE PRU/ml | Classes |
|---|---|---|---|---|---|---|---|
| A.A. | A.s. | Lolium P. | +++ | >17.5 | 4 | >17.5 | 4 |
| | RC.s. | Olea Eur. | ++− | 1.05 | 2 | 0.4 | 1 |
| | | Pariet. J. | ++− | 0.98 | 2 | 0.42 | 1 |
| | | Altern. T. | +++ | 4.68 | 3 | 0.77 | 2 |
| | | Mucor Ra. | − − − | <0.35 | 0 | 0.47 | 1 |
| F.F. | RC.s. | Lolium P. | ++++ | >17.5 | 4 | >17.5 | 4 |
| | A.s. | Dermat. P. | − − − | <0.35 | 0 | <0.35 | 0 |
| S.A. | A.c. | Dermat. P. | +++ | 14.5 | 3 | 15.35 | 3 |
| | | Pariet. O. | +++ | 14.8 | 3 | 15.11 | 3 |
| T.F. | A.c. | Dermat. P. | ++++ | >17.5 | 4 | >17.5 | 4 |
| | | Pariet. O. | − − − | <0.35 | 0 | <0.35 | 0 |
| S.R. | A.c. | Dermat. P. | +++ | 4.5 | 3 | 4.6 | 3 |
| | | Asperg. F. | − − − | <0.35 | 0 | <0.35 | 0 |
| S.R. | A.c. | Dermat. P. | +++ | >17.5 | 4 | >17.5 | 4 |
| | | Pariet. J. | − − − | <0.35 | 0 | <0.35 | 0 |
| T.R. | A.c. | Pariet. O. | +++ | 4.4 | 3 | 4.42 | 3 |
| | R.c. | Altern. T. | − − − | <0.35 | 0 | <0.35 | 0 |
| E.L. | A.c. | Dermat. P. | +++ | 3.6 | 3 | 4.14 | 3 |
| | R.c. | Lolium P. | ++++ | >17.5 | 4 | >17.5 | 4 |
| | | Pariet. J. | − − − | <0.35 | 0 | <0.35 | 0 |
| S.R. | RC.s. | Lolium P. | +++ | >17.5 | 4 | >17.5 | 4 |
| | | Olea Eur. | ++− | 0.35 | 1 | 0.35 | 1 |

TABLE 2c-continued

| Case | Symptoma-tology | Allergens | SPT | IgE in the serum PRU/ml | Classes | Nasal IgE PRU/ml | Classes |
|---|---|---|---|---|---|---|---|
| S.S. | RC.s. | Lolium P. | ++++ | 1.94 | 2 | 6.2 | 3 |
|  | A.s. | Pariet. J. | ++++ | >17.5 | 4 | >17.5 | 4 |

TABLE 2d

| Case | Symptoma-tology | Allergens | SPT | IgE in the serum PRU/ml | Classes | Nasal IgE PRU/ml | Classes |
|---|---|---|---|---|---|---|---|
| M.C. | R.s. | Lolium P. | ++++ | >17.5 | 4 | >17.5 | 4 |
|  |  | Olea Eur. | --- | <0.35 | 0 | <0.35 | 0 |
| M.F. | A.c. | Lolium P. | ++- | 4.69 | 3 | 1.62 | 2 |
|  | R.c. | Pariet. J. | ++- | <0.35 | 0 | 0.51 | 1 |
|  |  | Populus | --- | <0.35 | 0 | 1.6 | 2 |
|  |  | Dermat. P. | ++++ | >17.5 | 4 | 14.9 | 3 |
|  |  | Altern. T. | --- | <0.35 | 0 | 0.9 | 2 |
|  |  | Olea Eur. | ++- | <0.35 | 0 | <0.35 | 0 |
| B.D. | A.c. | Lolium P. | --- | <0.35 | 0 | 0.49 | 1 |
|  | R.c. | Dermat. P. | ++++ | 3.45 | 2 | 0.64 | 1 |
|  |  | Pariet. O. | --- | <0.35 | 0 | <0.35 | 0 |
| M.A. | A.s. | Lolium P. | +++ | >17.5 | 4 | 10.46 | 3 |
|  | RC.s | Pariet. J. | ++- | 0.8 | 2 | 0.57 | 1 |
|  |  | Olea Eur. | ++- | 0.8 | 2 | <0.35 | 0 |
|  |  | Dermat. P. | ++- | 1.91 | 2 | 0.71 | 2 |
|  |  | Altern. T. | --- | <0.35 | 0 | 0.69 | 1 |
|  |  | Cupress. | --- | 1.8 | 2 | 1.36 | 2 |
|  |  | Artemis. V. | --- | 0.58 | 1 | <0.35 | 0 |
| F.D. | A.c. | Lolium P. | +++ | >17.5 | 4 | 8.33 | 3 |
|  | R.c. | Poa Prat. | +++ | >17.5 | 4 | 4.17 | 3 |
|  |  | Artemim. V. | ++- | 1.46 | 2 | 1.36 | 2 |
|  |  | Olea Eur. | +++ | 4.41 | 3 | 1.45 | 2 |
|  |  | Pariet. J. | --- | 0.7 | 2 | 0.68 | 1 |
|  |  | Dermat. P. | ++- | <0.35 | 0 | 1.09 | 2 |
|  |  | Alterna. T. | +++ | 0.9 | 2 | 0.75 | 2 |
| M.M. | A.c. | Dermat. P. | ++- | 1.7 | 2 | 0.9 | 2 |
|  |  | Phleum P. | +++ | 1.8 | 2 | <0.35 | 0 |

TABLE 2e

| Case | Symptoma-tology | Allergens | SPT | IgE in the serum PRU/ml | Classes | Nasal IgE PRU/ml | Classes |
|---|---|---|---|---|---|---|---|
| B.MG. | A.c. | Dermat. P. | +++ | 0.57 | 1 | <0.35 | 0 |
|  | R.c. | Pariet. O. | ++- | 0.56 | 1 | 1.27 | 2 |
|  |  | Lolium P. | ++++ | 6.22 | 3 | 4.42 | 3 |
|  |  | Olea Eur. | ++- | 1 | 2 | 1.09 | 2 |
| A.A. | A.s. | Lolium P. | +++ | 2.59 | 2 | 1.2 | 2 |
|  | R.s. | Pariet. J. | +++ | 6 | 3 | 3.4 | 2 |
|  |  | Cynodo. D. | ++- | <0.35 | 0 | 2.5 | 2 |
|  |  | Dermat. P. | --- | <0.35 | 0 | 0.56 | 1 |
|  |  | Populus | --- | <0.35 | 0 | 0.53 | 1 |
|  |  | House D. | --- | <0.35 | 0 | <0.35 | 0 |
| A.M. | A.c. | Dermat. J. | --- | <0.35 | 0 | 1.00 | 2 |
|  |  | Dermat. P. | +++ | 17.5 | 4 | 6.26 | 3 |
| F.G. | A.c. | Pariet. O. | +++ | 0.95 | 2 | <0.35 | 0 |
|  |  | Dermat. P. | +++ | 0.95 | 2 | 1.07 | 2 |
| A.L. | RC.s. | Dermat. P. | +++ | 0.75 | 2 | <0.35 | 0 |
|  |  | Pariet. J. | ++- | <0.35 | 0 | 0.6 | 1 |
|  |  | Olea Eur. | ++- | <0.35 | 0 | 1.2 | 2 |
|  |  | Lolium P. | +-- | <0.35 | 0 | 0.35 | 1 |
| C.M. | RC.s. | Lolium P. | +++ | 0.9 | 2 | <0.35 | 0 |
|  |  | Pariet. J. | ++- | 0.4 | 1 | 0.43 | 1 |
|  |  | Populus | --- | 0.38 | 1 | <0.35 | 0 |
| T.M. | A.c. | Pariet. O. | --- | <0.35 | 0 | 0.42 | 1 |
|  | R.c. | Dermat. P. | +++ | 5 | 3 | >17.5 | 4 |
|  |  | Olea Eur. | --- | <0.35 | 0 | 0.38 | 1 |
| C.MR. | A.c. | Dermat. P. | ++++ | >17.5 | 4 | 14.8 | 3 |
|  | R.c. | Phleum P. | --- | <0.35 | 0 | 0.6 | 1 |

TABLE 2f

| Case | Symptoma-tology | Allergens | SPT | IgE in the serum PRU/ml | Classes | Nasal IgE PRU/ml | Classes |
|---|---|---|---|---|---|---|---|
| M.I. | A.c. | Dermat. P. | +++ | >17.5 | 4 | 0.89 | 2 |

TABLE 2f-continued

| Case | Symptoma-tology | Allergens | SPT | IgE in the serum PRU/ml | Classes | Nasal IgE PRU/ml | Classes |
|---|---|---|---|---|---|---|---|
| | | RC.c. | Pariet. J. | --- | 0.49 | 1 | 0.48 | 1 |
| | | Lolium P. | --- | <0.35 | 0 | <0.35 | 0 |
| L.S. | A.c. | Dermat. P. | +++ | >17.5 | 4 | 9.6 | 3 |
| | RC.c. | Lolium P. | --- | <0.35 | 0 | <0.35 | 0 |
| B.F. | A.s. | Lolium P. | ++- | 1.03 | 2 | 1.22 | 2 |
| | R.s. | Pariet. J. | ++- | 0.6 | 1 | 0.38 | 1 |
| G.A. | A.s. | Lolium P. | +++ | 12.5 | 3 | 2.38 | 2 |
| | RC.s. | Pariet. J. | ++++ | >17.5 | 4 | >17.5 | 4 |
| | | Olea Eur. | --- | <0.35 | 0 | <0.35 | 0 |
| | | Dermat. P. | --- | <0.35 | 0 | <0.35 | 0 |
| G.R. | A.c. | Dermat. P. | +++ | 3.49 | 2 | 0.57 | 1 |
| | R.c. | Pariet. J. | --- | <0.35 | 0 | <0.35 | 0 |
| S.R. | R.c. | Dermat. P. | ++++ | >17.5 | 4 | >17.5 | 4 |
| | | Pariet. J. | --- | <0.35 | 0 | <0.35 | 0 |
| L.E. | A.c. | Dermat. P. | +++ | 10.21 | 3 | 0.90 | 2 |
| | R.c. | Lolium P. | ++- | 8.3 | 3 | <0.35 | 0 |
| | | Pariet. J. | --- | <0.35 | 0 | <0.35 | 0 |
| | | Altern. T. | --- | <0.35 | 0 | <0.35 | 0 |
| M.C. | A.c. | Dermat. P. | ++++ | >17.5 | 4 | 12.71 | 3 |
| | R.c. | Asperg. F. | --- | <0.35 | 0 | <0.35 | 0 |
| Z.S. | A.c. | Dermat. P. | ++++ | >17.5 | 4 | 16.85 | 4 |
| | R.c. | Pariet. O. | --- | <0.35 | 0 | <0.35 | 0 |
| B.M. | A.c. | Dermat. P. | +++ | 0.35 | 1 | 5.31 | 3 |
| | R.c. | Pariet. J. | --- | <0.35 | 0 | <0.35 | 0 |
| T.F. | R.c. | Lolium P. | ++++ | >17.5 | 4 | <17.5 | 4 |
| | | Dermat. P. | +++ | 14.31 | 3 | 15 | 3 |

TABLE 2g

| Case | Symptoma-tology | Allergens | SPT | IgE in the serum PRU/ml | Classes | Nasal IgE PRU/ml | Classes |
|---|---|---|---|---|---|---|---|
| R.R. | A.c. | Dermat. P. | +++ | 6.97 | 3 | 0.77 | 2 |
| | | Egg White | --- | <0.35 | 0 | 1.03 | 2 |
| | | Milk | --- | <0.35 | 0 | <0.35 | 0 |
| | | Alfalact. | --- | <0.35 | 0 | <0.35 | 0 |
| | | Betalact. | --- | <0.35 | 0 | <0.35 | 0 |
| T.F. | RC.c.s. | Egg White | ++- | <0.35 | 0 | 0.41 | 1 |
| | | Betalact. | --- | <0.35 | 0 | <0.35 | 0 |
| | | Casein | ++- | <0.35 | 0 | 0.35 | 1 |
| | | Alfalact. | ++- | <0.35 | 0 | 0.35 | 1 |
| | | Phleum P. | ++- | <0.35 | 0 | 0.36 | 1 |
| | | Pariet. J. | --- | <0.35 | 0 | <0.35 | 0 |
| T.T. | R.s. | Phleum P. | --- | <0.35 | 0 | <0.35 | 0 |
| | | Pariet. O. | --- | <0.35 | 0 | <0.35 | 0 |
| A.O. | C.s. | Cynodo D. | --- | <0.35 | 0 | <0.35 | 0 |
| | | Pariet. O. | --- | <0.35 | 0 | <0.35 | 0 |
| | | Olea Eur. | --- | <0.35 | 0 | <0.35 | 0 |
| M.P. | C.s. | Phleum P. | --- | <0.35 | 0 | <0.35 | 0 |
| | | Olea Eur. | --- | <0.35 | 0 | <0.35 | 0 |
| | | Pariet. O. | --- | <0.35 | 0 | <0.35 | 0 |
| S.P. | RC.c. | Dermat. P. | --- | <0.35 | 0 | <0.35 | 0 |
| | | Altern. T. | --- | <0.35 | 0 | <0.35 | 0 |
| | | Egg White | --- | <0.35 | 0 | <0.35 | 0 |
| W.A. | A.c. | Dermat. P. | --- | <0.35 | 0 | <0.35 | 0 |
| | | Pariet. O. | --- | <0.35 | 0 | <0.35 | 0 |
| | | Altern. T. | --- | <0.35 | 0 | <0.35 | 0 |
| E.E. | C.s. | Lolium P. | --- | <0.35 | 0 | <0.35 | 0 |
| | | Pariet. J. | --- | <0.35 | 0 | <0.35 | 0 |
| L.S. | C.c. | Pariet. O. | --- | <0.35 | 0 | <0.35 | 0 |
| | | Dermat. P. | --- | <0.35 | 0 | <0.35 | 0 |
| | | Milk | --- | <0.35 | 0 | <0.35 | 0 |

TABLE 2h

| Case | Symptoma-tology | Allergens | SPT | IgE in the serum PRU/ml | Classes | Nasal IgE PRU/ml | Classes |
|---|---|---|---|---|---|---|---|
| V.R. | A.s. | Phleum P. | --- | <0.35 | 0 | <0.35 | 0 |
| | | Pariet. J. | --- | <0.35 | 0 | <0.35 | 0 |
| | | Olea Eur. | --- | <0.35 | 0 | <0.35 | 0 |
| | | Populus | --- | <0.35 | 0 | <0.35 | 0 |
| | | Planta. L. | --- | <0.35 | 0 | <0.35 | 0 |
| F.L. | C.c. | Dermat. P. | --- | <0.35 | 0 | <0.35 | 0 |
| | | Dermat. F. | --- | <0.35 | 0 | <0.35 | 0 |
| | | Pariet. O. | --- | <0.35 | 0 | <0.35 | 0 |

TABLE 2h-continued

| Case | Symptoma-tology | Allergens | SPT | IgE in the serum PRU/ml | Classes | Nasal IgE PRU/ml | Classes |
|---|---|---|---|---|---|---|---|
| | | Asperg. F. | - - - | <0.35 | 0 | <0.35 | 0 |
| | | Egg White | - - - | <0.35 | 0 | <0.35 | 0 |
| | | Milk | - - - | <0.35 | 0 | <0.35 | 0 |

TABLE 3

A comparison between two solid phases, i.e. polystyrene and paper, linked to the allergen, in six patients with concordantly positive specific IgE's nasal and in the serum

| | | | POLYSTYRENE | | PAPER | |
|---|---|---|---|---|---|---|
| Case | Allergen | S.P.T. | specific IgE in the serum | specific nasal IgE | specific IgE in the serum | specific nasal IgE |
| B.F. | Lolium p. | + + − − | 2 | 1 | 2 | 2 |
| | Parietaria | + + − − | 1 | 1 | 1 | 1 |
| G.R. | Derm. Pteron. | + + + − | 2 | 1 | 2 | 1 |
| T.F. | Lolium p. | + + + + | 4 | 3 | 4 | 4 |
| | Derm. Pteron. | + + + − | 3 | 3 | 3 | 3 |
| R.A. | Lolium p. | + + + + | 3 | 3 | 4 | 3 |
| S.R. | Derm. Pteron. | + + + − | 3 | 3 | 3 | 3 |
| C.A. | Phleum p. | + + + + | 4 | 2 | 4 | 3 |
| | Derm. Pteron. | + + + − | 2 | 2 | 3 | 3 |

TABLE 4

Total IgE determined by the PRIST - Incubation time 2 minutes - Patients 33

| Case | IgE in the serum (U/ml) | Nasal IgE (U/ml) |
|---|---|---|
| Z.S. | 570 | 4.3 |
| C.F. | 108 | 7.15 |
| B.M. | 108 | 11.4 |
| A.A. | 527 | 37.6 |
| M.F. | 900 | 50.5 |
| M.E. | 1866 | 33.6 |
| A.L. | 12(n.v.) | <0.5 |
| M.A. | 1000 | 73.6 |
| S.R. | 51.3 | <0.5 |
| P.C. | 1000 | 2.89 |
| C.A. | 45.7 | <0.5 |
| G.B. | 32(n.v.) | <0.5 |
| M.F. | 350 | 61.5 |
| B.F. | 71.5 | 2 |
| B.F. | 60.3 | 0.6 |
| C.F. | 1000 | 27.1 |
| R.E. | 71 | 31.7 |
| Z.M. | 280 | 0.7 |
| C.M. | 510 | 62.1 |
| M.I. | 209 | 2.2 |
| B.M. | 350 | <0.5 |
| P.C. | 36 | 2.3 |
| P.L. | 764 | 2.4 |
| D.S. | 940 | 4.5 |
| U.S. | 681 | 32.4 |
| C.B. | 75 | 3.9 |
| F.F. | 150 | 3.6 |
| C.M. | 12.4(n.v.) | <0.5 |
| L.S. | 42(n.v.) | <0.5 |
| M.B. | 46.05 | 0.5 |
| R.S. | 68 | <0.5 |
| P.F. | 10(n.v.) | <0.5 |
| P.F. | 108 | 17.3 |

IgE in the serum 2SD cases 28
Nasal IgE <0.5 cases 24
Concord. 87.8%
n.v. = Normal value.

The example of two cases is exposed in the following (see Table 2e, case B.MG and AL):

Case AL: the skin tests were positive for Dermatophagoide Pteronissinus only and the specific IgE in the serum were of the class 2 for the same allergen and not for the other ones; the nasal specific IgE, repeated twice, gave negative results for the Dermatophagoide Pteronissinus and they were positive on the contrary for Parietaria, Olea Eur. and Lolium P., in agreement with the nasal provoking tests and with the anamnesis; the patient who had been previously subjected to specific immunotherapy with Dermatophagoide Pteronissinus has received no benefit by the immunotherapy and showed the symptomatology during the pollen seasons.

Case B.MG: the skin tests were positive for Dermatophagoide Pteronissinus, Parietaria, Lolium P., Olea Eur., and the specific IgE in the serum showed positive results for the same allergens, respectively of the class 1 for the two first allergens and of the classes 3 and 2 for the other ones; the specific IgE of mucous membrane were on the contrary negative for Dermatophagoide and positive for the three other allergens in agreement with the nasal provoking tests as well as with the anamnesis.

The present invention has been disclosed with particular reference to some specific embodiments of the same but it is to be understood that modifications and changes can be introduced in the invention by those who are skilled in the art without departing from the spirit and scope of the invention for which a priority right is claimed.

What is claimed:

1. A mucous membrane allergy immunoassay test for the in situ determination of total IgE or an allergen specific IgE, said test being characterized in that it comprises the following operations:
   (a) contacting a mucous membrane surface in situ with at least one support to which an allergen or anti-IgE antibody has been immobilized;
   (b) contacting said support with the mucous membrane for a time period sufficient to form an immune complex between any IgE present on the mucous membrane surface and said allergen or said anti-IgE antibody;
   (c) recovering said support, and inserting the support into a test-tube and then performing a radioimmunological or an immunoenzymatic determination of the amount of total IgE or the allergen specific IgE on said support in said immune complex.

2. A mucous membrane allergy immunoassay test according to claim 1, wherein said in situ contacting time of stage (b) varies between about one minute and twenty minutes.

3. A mucous membrane allergy immunoassay test according to claim 1 or 2, wherein said determination of the amount of the total IgE or the allergen specific IgE is carried out on said support after storing the support of stage (c) for a time variable up to four months at a temperature of about −20° C.

4. A mucous membrane allergy immunoassay test according to claim 1 or 2, wherein said mucous membrane surface is the nasal mucous membrane.

5. A mucous membrane allergy immunoassay test according to claim 1 or 2, wherein said mucous membrane surface is the conjunctival mucous membrane or the rectal mucous membrane.

* * * * *

UNITED STATES PATENT AND TRADEMARK OFFICE
CERTIFICATE OF CORRECTION

PATENT NO. : 4,968,633
DATED : November 6, 1990
INVENTOR(S) : Francesco Marcucci It is certified that error appears in the above-identified patent and that said Letters Patent is hereby corrected as shown below:

Column 2, Line 40  "other immunoglobulins (IgE)"  it should be -- other immunoglobulins (IgG) --
Column 13:
Table 2e  "A.M.  A.c.  Dermat. J. "  it should be -- A.M.  A.c.  Pariet.  J. --

Column 10, Line 57  Please insert after Table 1 and before Table 2a the following:

|  |  |  |  |
|---|---|---|---|
| -- $\overline{X}$ | 2' | 5.40=5.14 | 2.08=1.69 |
|  | 5' | 9.64=5.34 | 2.32=2.09 |
|  | 10' | 9.24=5.44 | 2.63=2.24 |
|  | 30' | 9.03=5.78 | 3.02=2.81  -- |

Signed and Sealed this

Sixteenth Day of March, 1993

*Attest:*

STEPHEN G. KUNIN

*Attesting Officer*   *Acting Commissioner of Patents and Trademarks*